United States Patent
Tojo et al.

(10) Patent No.: US 9,682,249 B2
(45) Date of Patent: Jun. 20, 2017

(54) TRANSCRANIAL MAGNETIC STIMULATION SYSTEM

(71) Applicant: TEIJIN PHARMA LIMITED, Chiyoda-ku, Tokyo (JP)

(72) Inventors: Kenji Tojo, Hino (JP); Atsushi Asahina, Hino (JP)

(73) Assignee: Teijin Pharma Limited, Chiyoda-ku, Tokyo (JP)

( * ) Notice: Subject to any disclaimer, the term of this patent is extended or adjusted under 35 U.S.C. 154(b) by 157 days.

(21) Appl. No.: 14/353,688

(22) PCT Filed: Oct. 24, 2012

(86) PCT No.: PCT/JP2012/077523
§ 371 (c)(1),
(2) Date: Jul. 8, 2014

(87) PCT Pub. No.: WO2013/062021
PCT Pub. Date: May 2, 2013

(65) Prior Publication Data
US 2014/0343351 A1    Nov. 20, 2014

(30) Foreign Application Priority Data
Oct. 24, 2011   (JP) ................................. 2011-232883

(51) Int. Cl.
*A61N 2/02*   (2006.01)
*A61N 2/00*   (2006.01)

(52) U.S. Cl.
CPC ............... *A61N 2/02* (2013.01); *A61N 2/006* (2013.01)

(58) Field of Classification Search
CPC . A61B 19/5202; A61B 19/5212; A61B 19/54; A61B 19/5445; A61B 19/20; A61N 2/006; A61N 2/02
(Continued)

(56) References Cited

U.S. PATENT DOCUMENTS

| 3,116,365 A | 12/1963 | Prescott |
| 2003/0073899 A1 | 4/2003 | Ruohonen et al. |

(Continued)

FOREIGN PATENT DOCUMENTS

| EP | 2008687 A1 | 12/2008 |
| EP | 2444119 A1 | 4/2012 |

(Continued)

OTHER PUBLICATIONS

Communication dated Apr. 8, 2015 from the European Patent Office in counterpart application No. 12843321.6.
(Continued)

*Primary Examiner* — Samuel Gilbert
(74) *Attorney, Agent, or Firm* — Sughrue Mion, PLLC

(57) ABSTRACT

A compact and economical transcranial magnetic stimulation system has a magnetic field generator for generating a magnetic field to be used for providing magnetic stimulation to the head of patient. The generator has a magnetic coil for generating a variable magnetic field and a holder for holding the magnetic coil. The holder has positioning portions for positioning the holder against respective markings on the head of patient. The coil is placed into a suitable posture against certain position by aligning the positioning portions with the markings on the head of patient.

9 Claims, 11 Drawing Sheets

(58) Field of Classification Search
USPC .......................................... 600/13, 424, 426
See application file for complete search history.

(56) References Cited

U.S. PATENT DOCUMENTS

| | | | |
|---|---|---|---|
| 2004/0039279 | A1 | 2/2004 | Ruohonen |
| 2005/0025353 | A1* | 2/2005 | Kaneko .................. G06T 7/0004 |
| | | | 382/152 |
| 2005/0148808 | A1* | 7/2005 | Cameron ................ A61N 2/02 |
| | | | 600/13 |
| 2005/0193451 | A1 | 9/2005 | Quistgaard et al. |
| 2005/0234286 | A1* | 10/2005 | Riehl ..................... A61N 2/006 |
| | | | 600/9 |
| 2006/0122496 | A1 | 6/2006 | George et al. |
| 2006/0161039 | A1 | 7/2006 | Juliana et al. |
| 2006/0287566 | A1 | 12/2006 | Zangen et al. |
| 2007/0078466 | A1* | 4/2007 | Bodduluri ......... A61B 17/32053 |
| | | | 606/133 |
| 2008/0139871 | A1 | 6/2008 | Muntermann |
| 2008/0161716 | A1 | 7/2008 | Livne et al. |
| 2009/0187062 | A1 | 7/2009 | Saitoh |
| 2009/0216067 | A1* | 8/2009 | Lebosse ............... A61B 6/4441 |
| | | | 600/13 |
| 2009/0227830 | A1 | 9/2009 | Pillutla et al. |
| 2010/0036191 | A1 | 2/2010 | Walter et al. |
| 2011/0230701 | A1 | 9/2011 | Simon et al. |
| 2012/0157752 | A1 | 6/2012 | Nishikawa et al. |
| 2014/0179981 | A1 | 6/2014 | Katz et al. |

FOREIGN PATENT DOCUMENTS

| | | | | |
|---|---|---|---|---|
| IL | WO 2012059917 A1 * | 5/2012 | ............. A61B 19/54 |
| JP | H10-49218 A | 2/1998 | |
| JP | 11-197259 A | 7/1999 | |
| JP | 2003-180649 A | 7/2003 | |
| JP | 2004-636 A | 1/2004 | |
| JP | 2006102406 A | 4/2006 | |
| JP | 2006-320425 A | 11/2006 | |
| JP | 2007520290 A | 7/2007 | |
| JP | 2008505662 A | 2/2008 | |
| JP | 2008-528108 A | 7/2008 | |
| JP | 2008532722 A | 8/2008 | |
| JP | 2009-509671 A | 3/2009 | |
| JP | 2011-104385 A | 6/2011 | |
| WO | 03/098268 A1 | 11/2003 | |
| WO | 2007/041267 A2 | 4/2007 | |
| WO | 2007/123147 A1 | 11/2007 | |
| WO | 2009/063435 A1 | 5/2009 | |
| WO | 2010/147064 A1 | 12/2010 | |

OTHER PUBLICATIONS

Communication dated Apr. 8, 2015 from the European Patent Office in counterpart application No. 12844573.1.
International Preliminary Report of PCT/JP2012/077523, dated May 8, 2014.
International Preliminary Report of PCT/JP2012/077524, dated May 8, 2014.
Office Action issued by Japanese Patent Office in corresponding Japanese Patent Application No. 2011519757, dated Apr. 1, 2014.
International Search Report issued by the Japanese Patent Office in PCT application No. PCT/JP2010/059969, dated Jul. 6, 2010.
International Search Report of PCT/JP2012/077523, dated Dec. 4, 2012.
Communication dated Feb. 26, 2016, issued by the U.S. Patent and Trademark Office in counterpart U.S. Appl. No. 14/353,559.
Lebosse, Cyrille, Pierre Renaud, Bernard Bayle, Michel De Mathelin, Olivier Piccin, and Jack Foucher. "A Robotic System for Automated Image-guided Transcranial Magnetic Stimulation." 2007 IEEE/NIH Life Science Systems and Applications Workshop (2007): 55-58. Web. Feb. 18, 2016.
Office Action issued in U.S. Appl. No. 14/353,559, dated Oct. 11, 2016.

\* cited by examiner

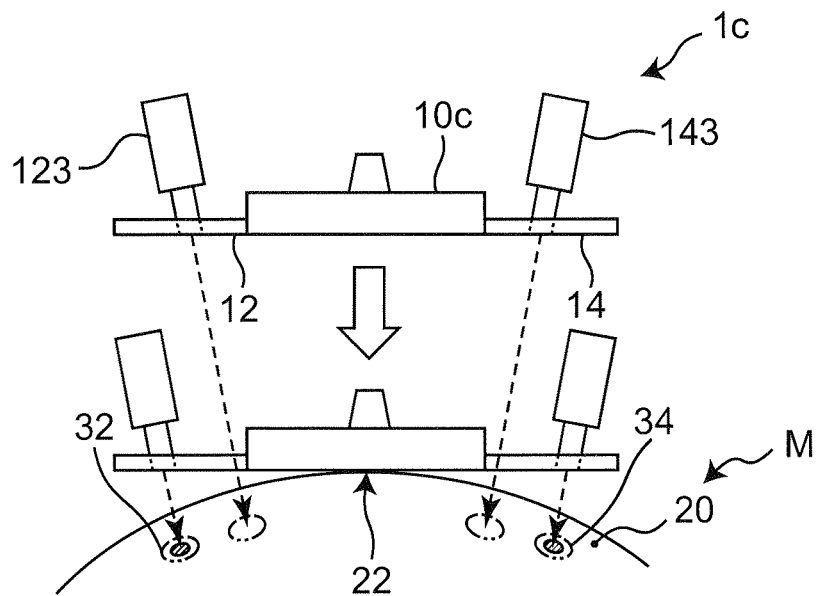
Fig.5A
Fig.5B
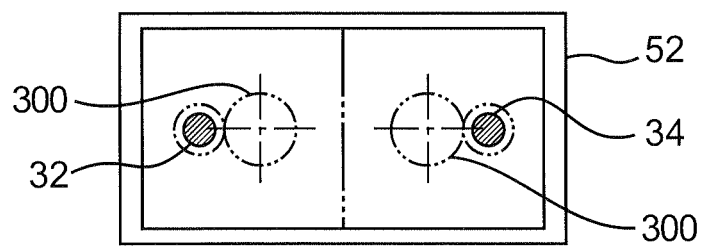
Fig.6A
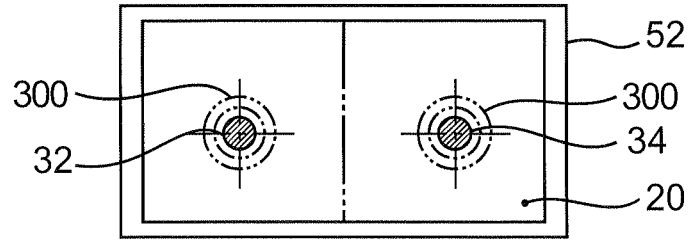
Fig.6B

TRANSCRANIAL MAGNETIC STIMULATION SYSTEM

CROSS REFERENCE TO RELATED APPLICATIONS

This application is a National Stage of International Application No. PCT/JP2012/077523 filed Oct. 24, 2012, claiming priority based on Japanese Patent Application No. 2011-232883 filed Oct. 24, 2011, the contents of all of which are incorporated herein by reference in their entirety.

TECHNICAL FIELD

The present invention relates to a transcranial magnetic stimulation system for applying magnetic stimulation to specific head portions of patients.

BACKGROUND OF THE INVENTION

Recently, an enhanced interest has been paid to the transcranial magnetic stimulation therapy for treating neurological patients for which drug treatments are not necessarily effective. The transcranial magnetic stimulation therapy is relatively a newly developed one which is effective in decreasing therapeutic stress of patients and/or symptoms by providing specific portions of brain such as cranial nerve with magnetic stimulation generated by the magnetic field generator positioned on the scalp of the patient.

Contrary to the conventional electric stimulation method which needs craniotomy procedure and uses indwelling electrodes which might be extremely uncomfortable to the patients, the transcranial magnetic stimulation is non-invasive and less stress and therefore is expected to be widely used.

Patent Literature 1 discloses a specific transcranial magnetic stimulation method for applying electric current to a coil mounted on or above the scalp of patient to generate local weak magnetic pulses, causing intracranial eddy current by electromagnetic induction to apply magnetic stimulation against the nerve cells in brain underneath the coil.

Patent Literature 1 also discloses that the transcranial magnetic stimulation method effectively relieves an intractable neuropathic pain and a suitable positioning of the local stimulation results in an increased pain-relief effect. It also discloses that the most effective stimulation point slightly varies from person to person.

This means that, an achievement of an increased therapy effect highly depends on how the optimum stimulation site is identified for each patient's head, i.e., how a precise positioning of the stimulation coil is attained on the patient's head. It is also known that the therapy effect can vary according to the orientation (posture) of the stimulation coil even if it is positioned at the same place.

Patent Literatures 2 and 3 disclose techniques for positioning the stimulation coils against the patient heads by using, for example, an optical tracking system using ultra infrared ray. This technology has been commercially available and also used in clinical applications. Patent Literature 4 discloses another apparatus for positioning the stimulation coil against the patient heads by using a multi jointed robot.

Patent Literature 1 further discloses that the effect of the transcranial magnetic stimulation therapy persists for about several hours and does not last up to several days. This means that, to attain an increased pain reduction effect, the transcranial magnetic stimulation therapy is desired to be applied regularly at smaller intervals, preferably every day, in order to reduce pain. Also, preferably the patient can take that therapy at the his or her home or in the neighborhood clinic in which his or her regular doctor is working with minimum physical and/or economical load.

CITATION LIST

Patent Literature

[Patent Literature 1] WO 2007/123147
[Patent Literature 2] JP 2003-180649 A
[Patent Literature 3] JP 2004-000636 A
[Patent Literature 4] 2006-320425 A

SUMMARY OF THE INVENTION

Technical Problem

Each of the conventional transcranial magnetic stimulation system with the coil positioning device is designed so that it is operated by skilled specialized physician and used for examination and/or research purpose in the relatively large hospital and/or research institution, so that it needs complicated operation, enhanced skill, enlarged space, and elevated cost. This results in that it is generally difficult for the patient, his or her family, or home doctor who may be unfamiliar with the operation of the system and imposes an enormous financial burden on the patient or relatively small clinic or hospital. In addition, it may also be difficult for them to secure a large space for the installation of the system.

For the reasons above, the patient has no other choice but to go to the large hospital with the transcranial magnetic stimulation and skilled physicians whenever he or she wants to undergo the transcranial magnetic stimulation therapy or to be admitted to such hospital, which practically results in that the patients have been forced to bear various burdens to take that therapy continuously.

Accordingly, the present invention is to provide a compact and economical transcranial magnetic stimulation system which is capable of providing a transcranial magnetic stimulation therapy routinely and continuously at patient's home or neighborhood home clinic without skill.

Solution to Problem

The transcranial magnetic stimulation system comprises a magnetic field generator for generating a magnetic field which is used for providing magnetic stimulation against a certain portion of patient's head, the magnetic field generator having a magnetic coil for generating a variable magnetic field and a holder for holding the magnetic coil, wherein the holder has a positioning portion for positioning the holder against a marking provided on the patient's head so that the coil can be positioned against the certain portion in a proper posture by aligning the positioning portion on the marking on the patient's head.

With the arrangement, the magnetic generator can easily be positioned against the marking provided on the certain portions of the patient. This allows the user of the transcranial magnetic stimulation system to position the magnetic field generator without special skill which has been needed conventionally.

The system further comprises a posture holding means for holding the coil in a suitable posture against the certain portion as the positioning portion is aligned with the marking on the patient head.

Preferably, the system comprises a recognition means for recognizing the marking.

Preferably, the recognition means comprises at least one imaging device provided adjacent the holder, allowing the coil to be held in the suitable posture by aligning the optical axis of the imaging device with the marking.

Preferably, the coil is held in the suitable posture against the certain position by rolling the imaging device about a contact between the patient head and the opposing lower surface of the holder to align the optical axis with the marking.

Preferably, the system comprises an optical device provided adjacent the imaging device and capable of emitting directional light beam, wherein the coil is held in the suitable posture against the certain position by aligning an intersection of the optical axis of the optical device and the optical axis of the imaging device with the marking.

More preferably, the system comprises
a moving mechanism for moving the holder on and along the head surface of patient;
a recognition means for recognizing the marking;
a controlling means for controlling the moving mechanism in accordance with the output from the recognition means to automatically position the positioning portion against the marking.

The marking may be made of a pattern applied on the head surface of patient, an object attached on the head surface of patient, or an object implanted under the head surface of patient.

The object may be means for generating a magnetic field and the recognition means is means for detecting the magnetic field. The object may be means for generating radio or some wireless signal and the recognition means is means for detecting the radio signal. The object may have a visible configuration and the recognition means is means for visibly recognizing the object configuration.

Advantageous Effects of Invention

According to the invention, the patient can perform the transcranial magnetic stimulation therapy routinely and repeatedly in, for example, his or her house or a neighborhood primary-care medical facility. The system can be operated easily by the patient, his or her family, or neighborhood primary-care doctor or assistance even though they are not experts of this system. Also, comparing the conventional space-occupying and costly system, the invention is less expensive and occupies less space so that it can be installed in a private patient's house or relatively small office or clinic.

BRIEF DESCRIPTION OF THE DRAWINGS

FIGS. 5A and 5B are views showing a second modification of the first embodiment of the transcranial magnetic stimulation system according to the first embodiment of the invention;

FIGS. 6A and 6B are views corresponding to FIGS. 5A and 5B, showing a positioning procedure made for the second modification of the first embodiment of the transcranial magnetic stimulation system;

PREFERRED EMBODIMENT OF THE INVENTION

Referring to the accompanying drawings, an exemplary embodiment of the transcranial magnetic stimulation system according to the invention will be described below. In the following descriptions, the discussions are made to the transcranial magnetic stimulation system which is preferably used for medical treatment in the departments of neurosurgery and neurology; however, it may be applied similarly to the medical treatment in other departments of, such as, psychosomatic and psychiatry for treating patient suffering from depression.

Although direction- and position-related terminologies such as upper and lower surfaces are used for the better understanding of the invention in the following descriptions, a technical scope of the invention should not be restrictively construed by the meanings of those terms. Also, the following descriptions relate to the specific embodiment of the invention and do not intend to limit its application.

In the following descriptions, a "posture of stimulation coil" means an orientation of the stimulation and the orientation angle of the stimulation coil, an "orientation of coil" an orientation of coil with respect to a patient's scalp, and an "angle of stimulation coil" an angle between a normal line from the patient's scalp and a direction of magnetic field. Also, the term "attach(ed)" to the patient's scalp implies "partly color(ed)", "implant(ed)", or "adhere(d)" on the patient's scalp.

Figure 1:
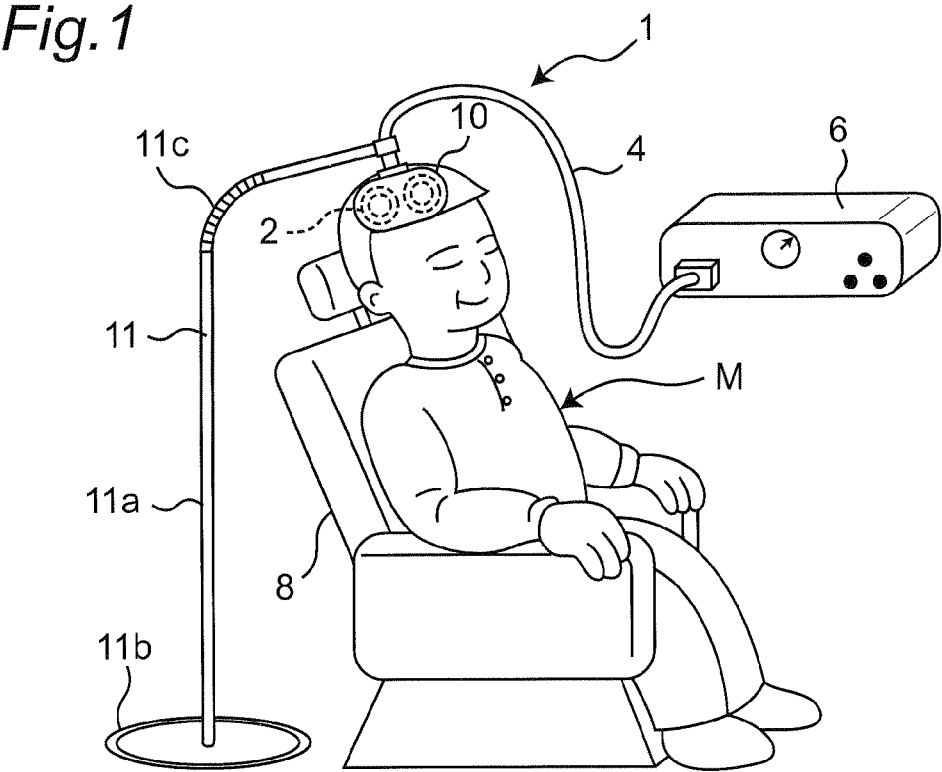
FIG. 1 is a schematic view showing a general construction of a transcranial magnetic stimulation system of the invention.

As shown in FIG. 1, the transcranial magnetic stimulation system (hereinafter referred to as "magnetic stimulation system", generally indicated at 1, includes a stimulation coil (magnetic field generation means) 2 and a magnetic stimulation control unit 6 electrically connected to the stimulation coil 2 through a cable 4. The magnetic stimulation system 1 is designed to treat and/or ease certain symptoms by applying magnetic stimulation with certain intensity into the cranial nerve of the patient M by means of the stimulation coil 2 positioned on the scalp of the patient M sitting on a seat 8 for treatment.

As shown in the drawing, a coil holder 10 holding the coil 2 is secured at a distal end of a holder fixture (posture holding means) 11. The holder fixture 11 includes a standing pole 11a and a base 11b. A part of the standing pole 11a, adjacent the distal end of the holder fixture 11, is made of a metallic flexible tube 11c, allowing the coil 2 to be positioned in an optimal position simply by holding and moving the coil holder 10 onto a predetermined position on of the scalp of the patient M. The positioning of the stimulation coil 2 against the scalp of the patient M will be described later.

The stimulation coil 2 is designed so that it can generate variable magnetic field which applies the magnetic stimulation onto at least specific positions of the patient M. Various types of conventional magnetic coils are available for the stimulation coil 2. In this embodiment, the stimulation coil 2 is a so called eight-shape coil having a configuration made by placing two spiral coils on the same plane in the form of number eight. This allows that an application of electric current to this eight-shaped coil in the same direction as shown in the drawing, for example, generates the maximum inductive current density immediately beneath the overlapped potions of the spirals. Although this stimulation coil or magnetic coil 2 may be relatively difficult to be held in a desired posture, it is advantageous to concentrate the magnetic stimulation in a certain site.

Figure 2:
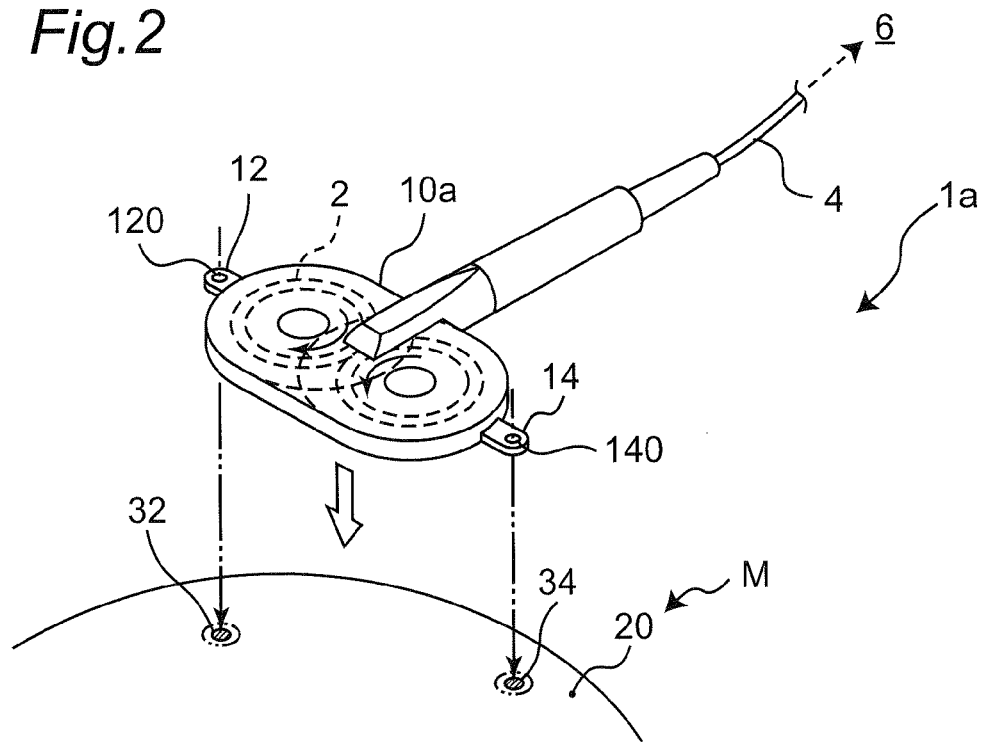
FIG. 2 is a perspective view showing a coil holder of the transcranial magnetic stimulation system according to the first embodiment of the invention.

As shown in FIGS. 1 and 2, the stimulation coil 2 is assembled in the coil holder 19 in the form of oval. Specifically, the coil holder 10 is made by molding non-magnetic resin material and the stimulation coil 2 is integrally formed with the coil holder 10 at the molding of the coil holder. Preferably, the bottom surface of the coil holder, facing the scalp of the patient M, has a concave spherical surface formed therewith, corresponding to an outer configuration of the head of the patient M. This allows that the coil holder 10 to be moved smoothly on the head surface 20 of the patient M. It should be noted that the planar configuration of the coil holder 10 may have ellipsoidal or egg-shaped configuration such as oval.

The magnetic stimulation control unit 6, which is designed to control an application of electric current pulses to the stimulation coil 2, may use any one of conventional units. The control unit 6 is operated by an operator. In the operation, the operator can control various settings such as magnitude and/or waveform of the current pulses determining the intensity of magnetic stimulation and/or the stimulation cycle or interval.

As described in the background, an enhanced pain reduction effect can be obtained by properly concentrating the magnetic stimulation from the coil provided on the patient's scalp on the targeted cranial nerve thereunderneath. Therefore, the optimum coil position and posture for each patient where the maximum reduction effect of neuropathic-pain would be obtained by the application of magnetic stimulation is determined at the time of initial diagnostic test by using a dedicated positioning device including a coil unit similar to the coil holder 10 in the medical institution. Through this test, an object or marking for positioning is attached or formed on the scalp or skin of the patient in order for allowing the optimum coil position and posture to be reproduced in the next therapy.

Preferably, the position of marking is provided at a different location away from the optimum coil position so that it can be viewed directly or indirectly to recognize that the coil holder 10 is properly positioned on the head with respect to the marking. At least one marking is provided. For the purpose of precise positioning, a plurality of markings are preferably provided. The shape of the marking is not limited to a simple dot pattern and it may be a two-dimensional pattern such as line. In the latter case, only one marking may be sufficient for the positioning.

The marking may be an additional object or attachment such as a pattern painted on a part of the patient's scalp or anything physically attached on or implanted in the patient's scalp, such as piece of metal (e.g., titanium), piece of magnet, RFID, IC tag, or pierce or a non-additional object or immovable or less-movable reference portion of patient's body such as tail of eye, ear, glabella, or tooth. The marking pattern painted on the scalp may take any configuration such as circle, square, rectangular, elongated rectangular, or triangle. Glue is preferably used for attaching the object such as metal piece on the scalp. The object or the metal piece may be attached to the patient's hair. In this instance, metal piece may be attached by using glue or by tangling it in the patient' hair. Instead, a hair implantation technique may be used in which marking hair stained in different color than the patient's hair color is tangled at the root of his or her hair. The marking may be made by sewing or implanting bioabsorbable polymer member such as bioabsorbable suture or bone securing material mad of polylactic resin, for example, on or in the patient's skin in a visible manner. Alternatively, the marking may be made directly on the patient's skin by using moxa cautery.

The marking pattern may be made by stamping in a certain ink or fixing a certain dye or colorant on the patient's skin or placing a certain dye or colorant in or under the skin by means of permanent cosmetics, for example. Of course, the dye or colorant should be harmless. A vegetable origin colorant such as henna may be used for this purpose.

Depending on the marking method or marking material such as dye or colorant, the marking can be maintained for several weeks, years, or almost semipermanently. This means that a suitable method may be selected in accordance with the duration of the therapy. For example, the marking made of bioabsorbable suture or bone securing material can be used for about three months until it is decomposed within the patient's body.

Preferably, the color of the pattern is less-distinguishable but visible in the hair, such as purple or navy-blue.

Descriptions will be made to embodiments of the magnetic stimulation system 1, allowing the marking or markings on the patient's scalp to be recognized easily and then the system to be positioned properly with respect to the marking or markings without difficulty.

First Embodiment

FIG. 2 shows an embodiment of the coil holder 10a which is designed to be positioned against the markings 32 and 34 painted or attached on respective portions of the scalp 20 of the patient M. As shown in the drawing, the coil holder 10a has two positioning projection 12 and 14 (portions of the positioning means) provided on the edges of the opposite sides thereof on the longitudinal axis extending in a direction passing through the centers of two spiral coils. The projections 12 and 14 extend substantially in parallel to the top and bottom surfaces of the coil holder 10a. The projections 12 and 14 have apertures 120 and 140 (portions of the positioning means), respectively, defined therein. A distance between the centers of the apertures 120 and 140 is designed to be equal to that of the markings 32 and 34. As described above, the optimum coil position to the patient is determined by using the same coil holder and the markings 32 and 34 are provided on respective positions corresponding to the marking apertures of the coil holder positioned on the patient's head at the initial diagnostic test in the medical institution.

The coil holder 10a so constructed is positioned so that the apertures 120 and 140 places on the markings 32 and 34, respectively, on the head surface 20 of the patient M, causing the coil 2 to be properly positioned at the optimum coil position. The metal flexible tube 11c forming a part of the holder fixture 11 permits the coil holder 10a to be oriented to take a desired posture to a certain extent. Also, the coil holder 10a is maintained in a stable manner with its apertures 120 and 140 positioned on the respective markings 32, 34.

According the magnetic stimulation system 1a, the coil holder 10 is mounted on the optimum coil position relative to the markings 32 and 34 without difficulty. The number of projections 12 and 14 is not limited to two and it can be varied in accordance with the number of the markings.

Figure 3:
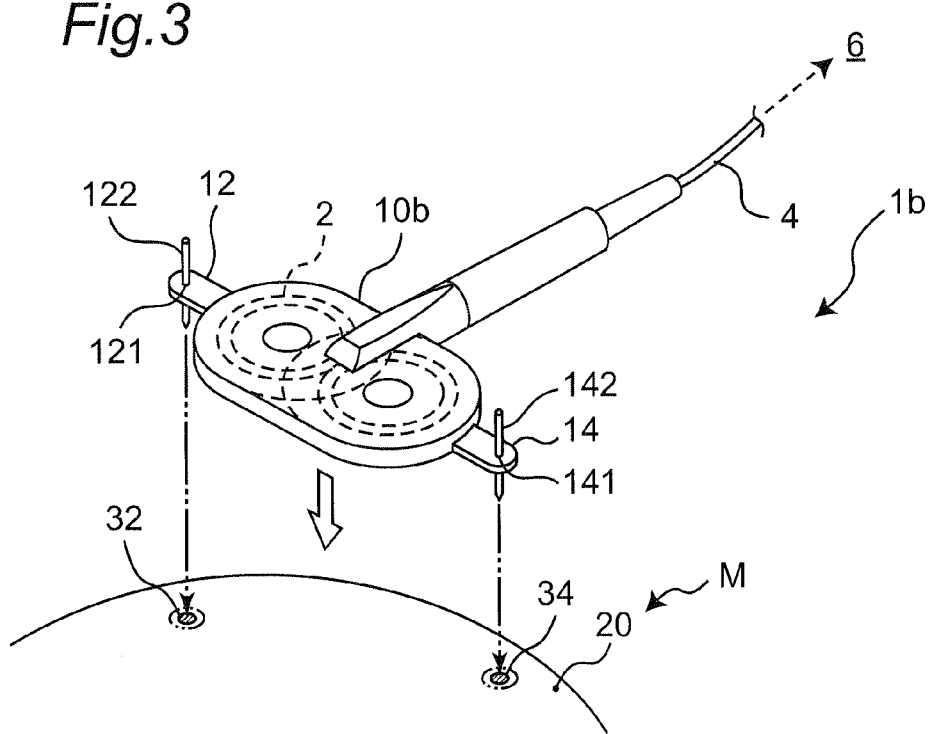
FIG. 3 is a perspective view showing a modified coil holder of the transcranial magnetic stimulation system according to the first embodiment of the invention.

FIG. 3 shows another embodiment of the coil holder. Portions of the coil holder 10b of this embodiment are indicated by like reference numerals used for the coil holder 10a in the previous embodiment in order to prevent duplicate discussions in the following descriptions. As shown in the drawing, according to the coil holder of this embodiment the positioning projections 12 and 14 are formed with threaded holes 121 and 141, instead of apertures 120 and 140, in which the guiding threaded rods 122 and 142 (portions of the positioning means) are engaged.

Figure 16:
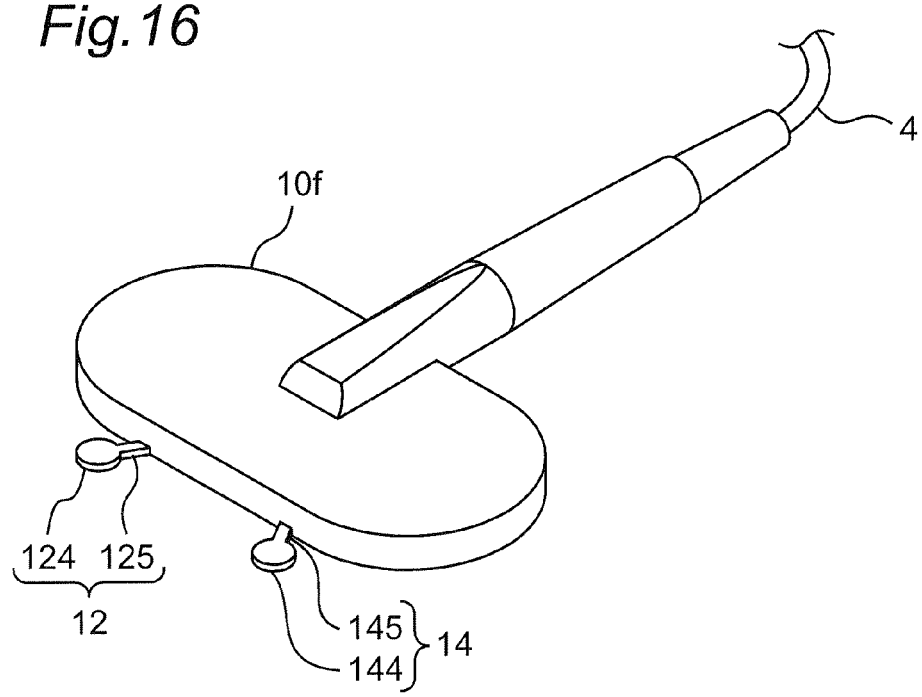
FIG. 16 is a perspective view showing another modification of the first embodiment of the transcranial magnetic stimulation system according to the invention.

According to this embodiment, the positioning of the coil holder 10b to the markings 32 and 34 is attained simply by positioning the distal or lowermost ends of the guiding rods 122 and 142 on the respective markings 32 and 34. Also, rotating the guide rods in the clockwise or counterclockwise direction allows the coil holder 10b to be positioned at the optimum height, at the optimum angle, and in the optimum orientation. Preferably, three threaded holes and associated positioning projections are provided to facilitate the adjustments of height, angle, and orientation. Once the coil holder 10b has been positioned at the optimum position, the guide rods 122 and 142 may be removed from the coil holder 10b FIG. 16 shows another embodiment of the coil holder. According to the coil holder 10f of this embodiment, like parts of the coil holder are indicated by like reference numbers used for the coil holder 10a shown in FIG. 2. As shown in the drawing, the positioning projections 12 and 14 of the coil holder 10f include distal end portions 124 and 144 having the same configuration as the markings (circular configuration), and arms 125 and 145 connecting the circular portions 124 and 144 to the coil holder 10e. The distal end portions 124 and 144 may have a configuration similar to or different from that of markings.

Although the projections provided on the coil holder are used for the positioning portions in the previous embodiments, other configurations such as cutout, concaved, or convex portions formed on the outer periphery of coil holder may be used for the positioning portions instead.

Although the coil holder are placed at the optimum position by the helper, it may be positioned at that position by the patient without help by, for example, viewing a mirror provided on the bottom portion of the coil holder or viewing images captured by a camera (CCD or CMOS camera) provided thereon. The camera positioned at the projection 12, 14, the marking aperture 120, 140, or circular portion 124, 144 produces less disparity compared to the visual viewing, ensuring a precise positioning with an increased reproducibility.

First Modification

Figure 4:
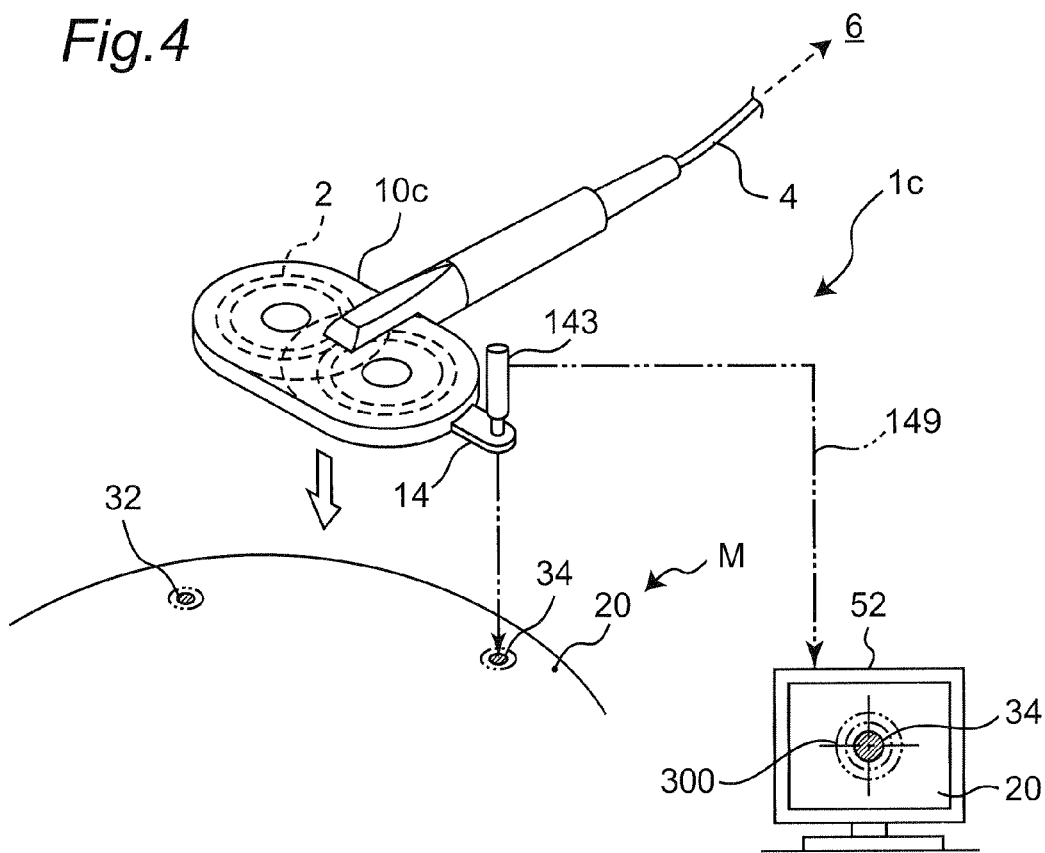
FIG. 4 is a view showing a coil holder of the first modification of the transcranial magnetic stimulation system according to the first embodiment of the invention.

Referring to FIG. 4, a first modification will be described below. In this modification, the projection 14 is provided at one edge of the coil holder 10c on the longitudinal axis thereof so that it extends substantially in parallel to the upper and bottom surfaces of the coil holder 10c. The distal end of the projection 14 securely holds a camera 143 so that the optical axis of the camera 143 is oriented substantially vertically to the upper and bottom surfaces of the coil holder 10c. The camera 143 is electrically connected through a communication cable 149 to a display 52 so that images captured by the camera 143 are shown on the display 52 by using image signal transmitted from the camera 143 to the display 52. According to the arrangement, the patient or the helper can place the coil 2 of the coil holder 10c at the optimum coil position by moving the coil holder 10c so that the marking 34 (32) aligns with the collimation mark 300 of the camera 143 while viewing the relative positions thereof on the display 52. In this modification, the collimation mark 300 is made of cross hairs of horizontal and vertical lines and the crossing point of the horizontal and vertical lines is positioned on the optical axis of the camera 143. The collimation mark 300 is not limited to the cross hairs and it may be circular or rectangular pattern, for example, in which the positioning of the coil holder may be made so that the center of the pattern aligns with the optical axis of the camera. These positioning operations are likewise applied to other embodiments which will be described below.

Second Modification

FIG. 5 shows a second modification in which two cameras 123,143 are provided at opposite ends of and on the longitudinal axis of the coil holder 10c. Specifically, coil holder 10c has at its opposite ends and on its longitudinal axis a pair of projections 12 and 14 extending substantially in parallel to the upper and lower surfaces of the coil holder 10c. The projections 12 and 14 hold respective cameras 123 with the optical axes thereof angled with the upper or lower surfaces of the coil holder 10c.

In operation of the magnetic stimulation system 1c according to the second modification, the patient or the helper places the coil 2 of the coil holder 10c at the optimum coil position by moving the coil holder 10c so that the markings 32 and 34 align with the collimation marks 300 of the cameras 123 and 143, respectively, while viewing the relative positions thereof on the display 52. As shown in FIG. 6A, if the coil holder 10c takes a position shown in FIG. 5B which is away from the optimum coil position shown in FIG. 5B, the left and right markings 32 and 34 appear on the left and right sides of the left and right collimation marks 300 of the cameras 123 and 143, respectively. The patient or helper moves the coil holder 10c toward the head surface 20 of the patient M as shown in FIGS. 5A and 5B until the markings 32 and 34 align with the collimation marks 300 of the cameras 123 and 143, respectively, as shown in FIG. 6B while viewing relative positions thereof on the display 52. This results in that the coil holder 10c is mounted at the optimum coil position when the collision marks 300 of the cameras 123 and 143 are placed on the markings 32 and 34, respectively. As described above, according to the second modification the patient or the helper can position the coil holder 10c at the optimum position precisely while viewing the displacement of between the optical axes of the cameras 123 an 143 and the marking 32 and 34 on the display 52.

Third Modification

Figure 7A:
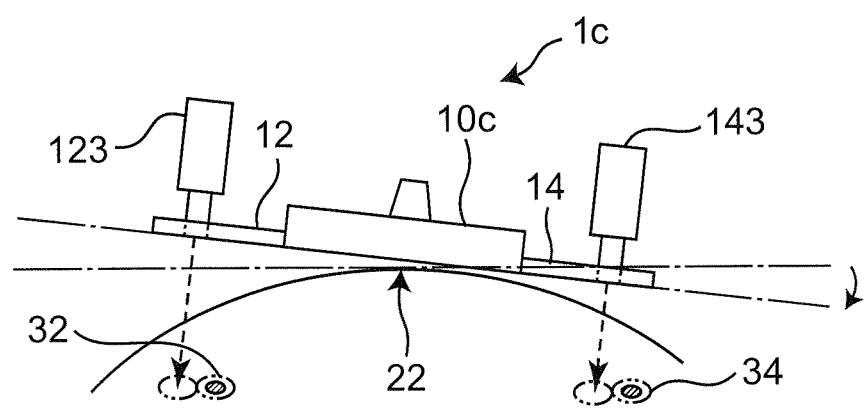
FIGS. 7A and 7B are views showing a positioning procedure made for the third modification of the first embodiment of the transcranial magnetic stimulation system.
Figure 7B:
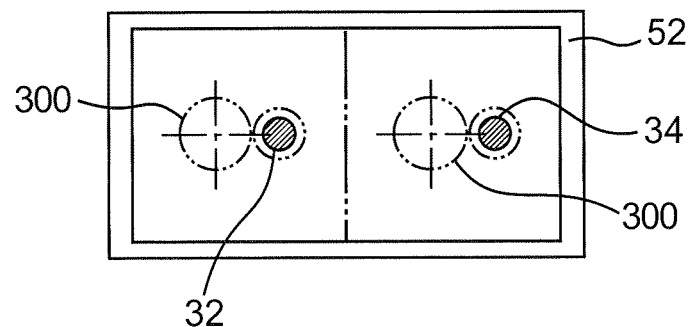
Figure 8A:
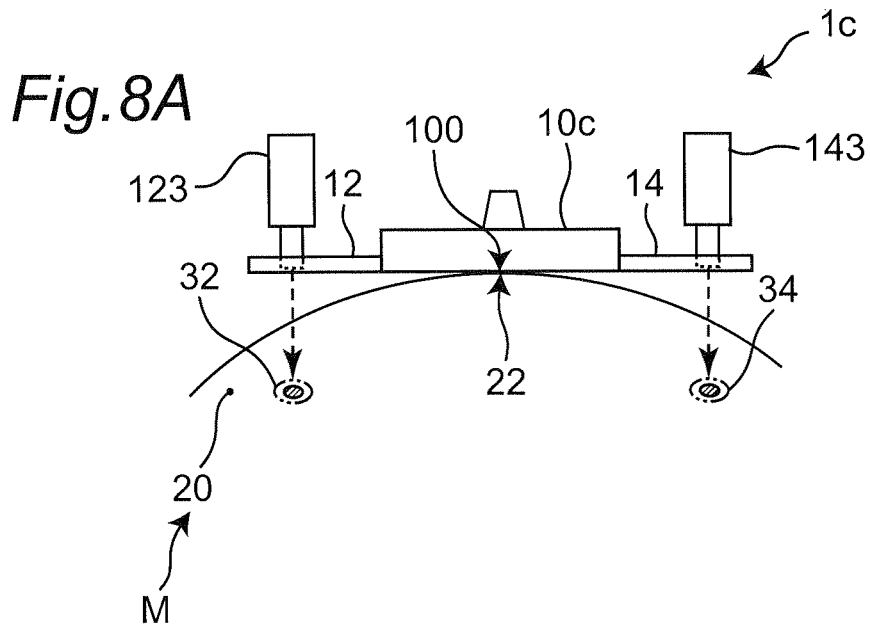
FIGS. 8A and 8B are views, corresponding to FIGS. 7A and 7B, showing the positioning procedure made for the third modification of the first embodiment of the transcranial magnetic stimulation system.
Figure 8B:
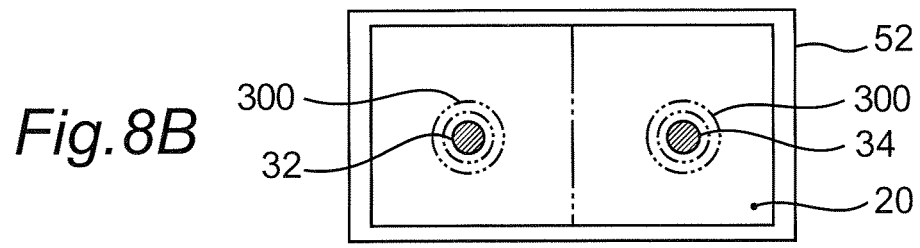

FIGS. 7 and 8 show a third modification. Preferably, in this modification the coil holder 10c is oriented by rolling it about a contact 100 between the top 22 of the head of the patient M and the opposing lower surface of the coil holder 10c. For this purpose, the projections 12 and 14 are mounted at the opposite ends and on the longitudinal axis of the coil holder 10c and extended substantially in parallel to the upper and lower surfaces of the coil holder 10c. Also, the cameras 123 and 143 are securely held by the projections 12 and 14 with their optical axes oriented substantially orthogonal to the upper and lower surfaces of the coil holder 10c.

In positioning, as shown in FIG. 7A the patient or M or the helper places the coil holder 10c in a position adjacent the optimum coil position. For example, as shown in the drawing the markings 32 and 34 may take positions located on the left or right side of the left and right collimation marks 300 of the cameras 123 and 143, respectively. Therefore, as shown in FIGS. 7A and 8A, the patient or M or the helper positions the coil holder 10c at the optimum coil position by rolling it about a contact 100 between the top 22 of the head of the patient M and the opposing lower surface of the coil holder 10c so that the markings 32 and 34 align with the collimation marks 300 of the cameras 123 and 143 on the display 52, respectively, while viewing the relative positions thereof on the display. The coil holder 10c may be moved along the head surface 20 as necessary.

Fourth Modification

FIG. 9 shows a fourth modification. In this modification, the projection 14 is securely mounted on one end of and on the longitudinal axis of the coil holder 10c and extended substantially in parallel to the upper and lower surfaces of the coil holder 10c. The proximal end portion of the projections 14 securely holds the camera 143 with the optical axis of the camera 143 oriented substantially orthogonal to the upper and lower surfaces of the coil holder 10c. The distal end portion of the projection 14 securely holds an optical device or laser beam oscillator 150 with its optical axis angled with the upper and lower surfaces of the coil holder 10c.

Figure 9A:
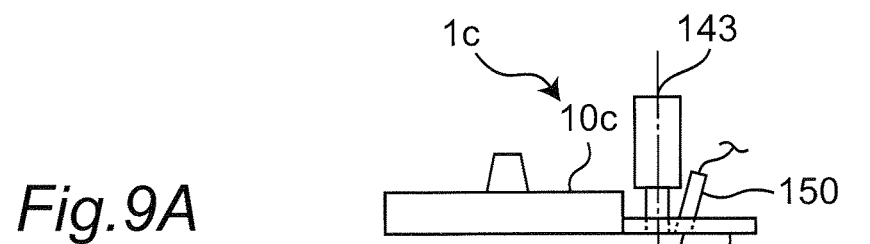
FIGS. 9A and 9B are views showing a positioning procedure made for the fourth modification of the first embodiment of the transcranial magnetic stimulation system.
Figure 9B:
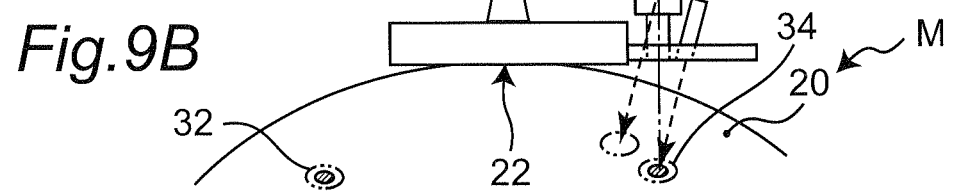
Figure 10A:
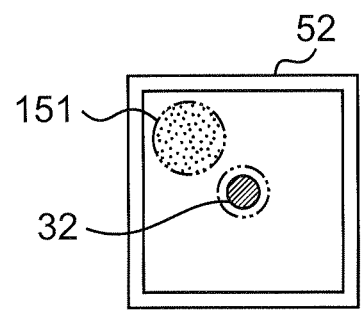
FIGS. 10A and 10B are views, corresponding to FIGS. 9A and 9B, showing the positioning procedure made for the fourth modification of the first embodiment of the transcranial magnetic stimulation system.
Figure 10B:
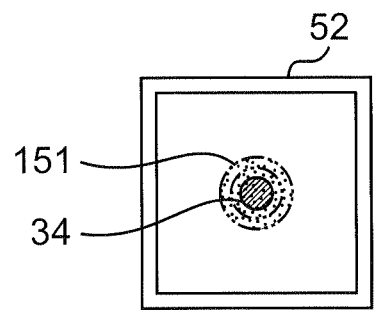

In operation of the magnetic stimulation system 1c, the patient or helper places the coil holder 10c adjacent the optimum coil position and then moves it so that the laser spot 151 aligns on the marking 34 while viewing the relative positions thereof on the images captured and shown on the display 52. For example, as shown in FIG. 9A, when the coil holder 10c takes a position which is displaced away from the optimum coil position, the laser spot 151 is in a position which is part of the left side toward the contact point 22. In this situation, as shown in FIGS. 9A and 9B the patient or helper moves the coil holder 10c toward the head top 20 of the patient M until the laser spot 151 of the laser beam oscillator 150 aligns with the marking 34 (see FIG. 10B) while viewing the relative positions thereof on the display 52. The coil holder 10c is positioned at the optimum coil position when the laser spot 151 of the laser beam oscillator 150 aligns with the marking 34. As above, according to the fourth modification which uses the displacement of between the laser spot 151 and the marking 34 the patient or the helper can positions the coil holder precisely while viewing the display 52. Although in the modification one the camera 143 and the laser beam oscillator 150 are provided at one longitudinal end of the coil holder 10c, they may also be provided on the opposite end of the coil holder 10c.

Although the laser beam oscillator 150 is indicated as one modification of the optical devices, it may be other device capable of emitting directional light or beam. Rather than light emitting diode (LED), other optical device may be used which employs a light source for emitting diffusion light and a lens unit positioned ahead of the light source for forming the diffusion light from the light source into directional light.

Fifth Modification

Figure 11:
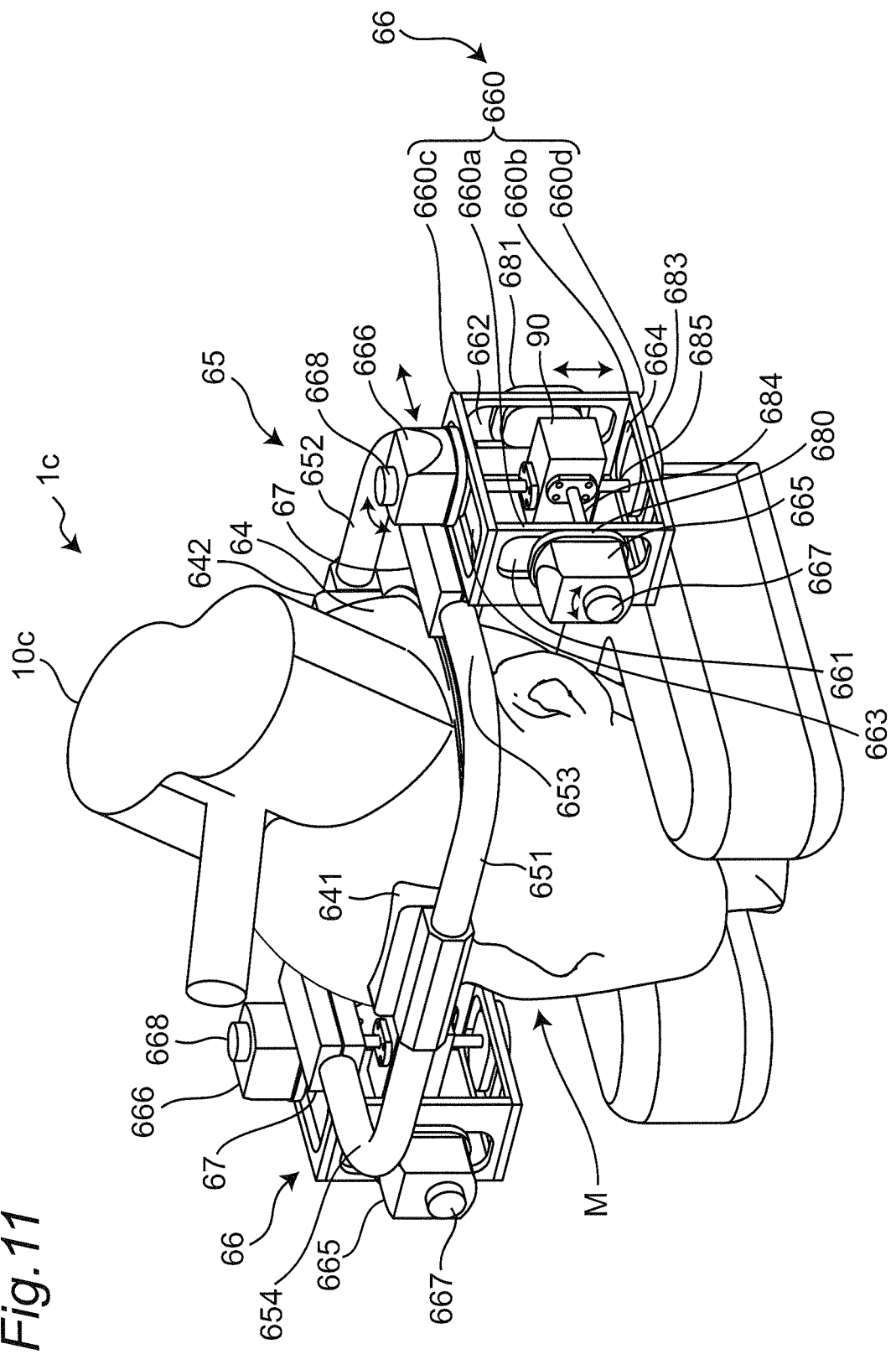
FIG. 11 is a perspective view showing a fifth modification of the first embodiment of the transcranial magnetic stimulation system.

FIG. 11 shows a magnetic stimulation system 1c which is a more specific modification of the fourth modification. The magnetic stimulation system 1c has a helmet 64 having an internal configuration similar to the outline of the head surface 20 of the patient M (see FIG. 2 for example). Preferably, the helmet 64 is made of non-magnetic polymer material. The coil holder 10c with the stimulation coil (not shown) is assembled in the helmet 64. The position of the coil holder 10c relative to the helmet 64 is determined so that the coil holder 10c takes the optimum coil position when the patient M wears the helmet 64.

The magnetic stimulation system 1c has a horizontal frame 65 surrounding the helmet 64. The horizontal frame 65 includes frame portions 651, 652, 653, and 654 positioned on front, rear, left and right sides of the helmet 64. In the modification, the front and rear frame portions 651 and 652 are fixed to the helmet 64 by fixing members 641 and 642. Similar to or in addition to the front and rear frame portions 651 and 652, the left and right frame portions 653 and 654 may be fixed to the helmet 64.

Each of the left and right frame portions 653 and 654 supports means for marking recognition or a recognition unit 90. The marking recognition unit 90 includes a box-like housing 160 shown in FIG. 3 for accommodating a camera 143 for imaging a marking (not shown) provided on the mastoid which is a convex portion existing on the rear side of ear, for example, and a light source made of laser beam oscillator 150 for emitting light ray in a direction obliquely crossing the optical axis of the camera in order to establish a suitable distance between the camera 143 and the marking. The housing 160 constructed above is supported by an adjustment mechanism 66 with openings for the camera 143 and the laser beam oscillator 150 exposed to the patient.

Figure 12:
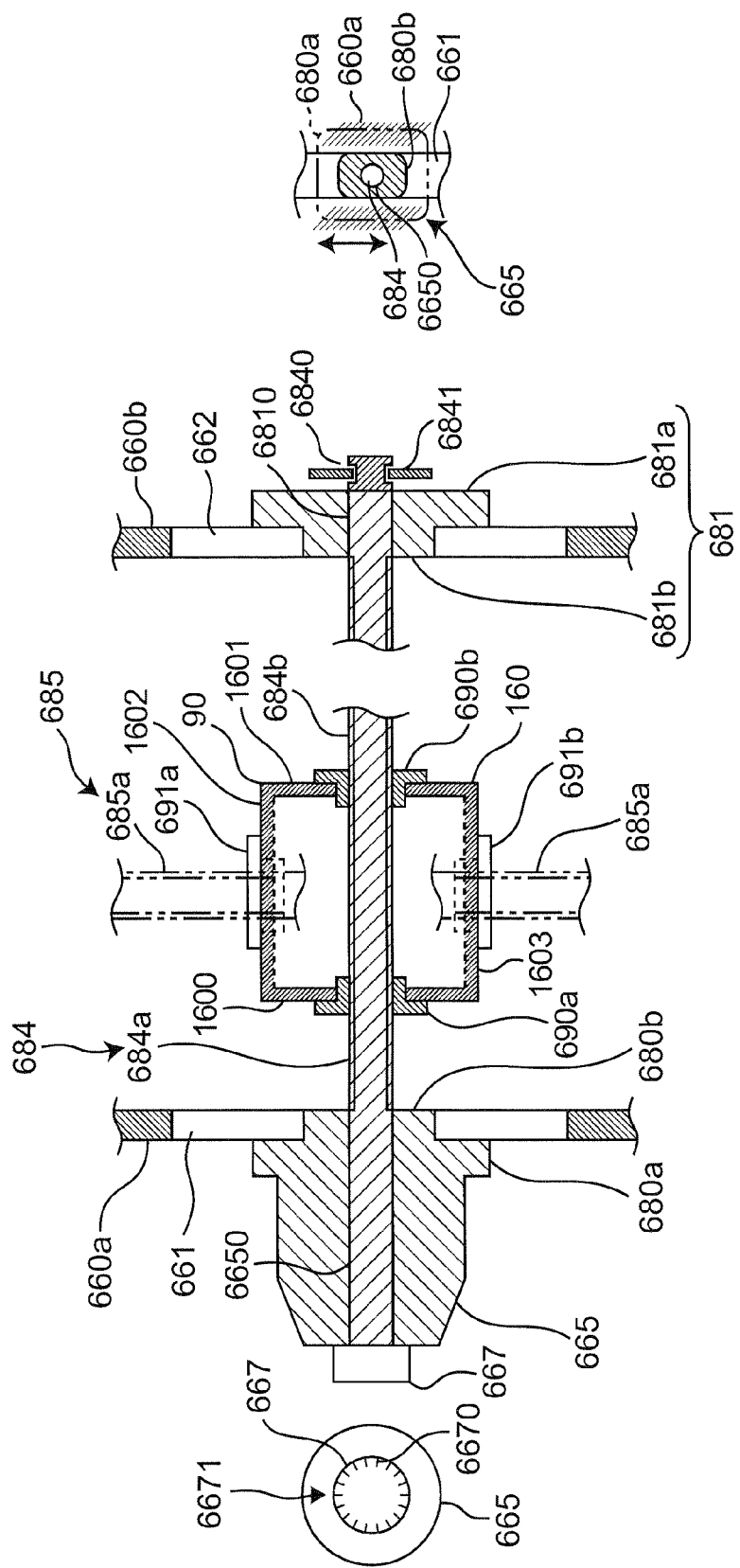
FIG. 12 is an exploded view of an adjustment mechanism in the fifth modification of the first embodiment of the transcranial magnetic stimulation system.
Figure 13:
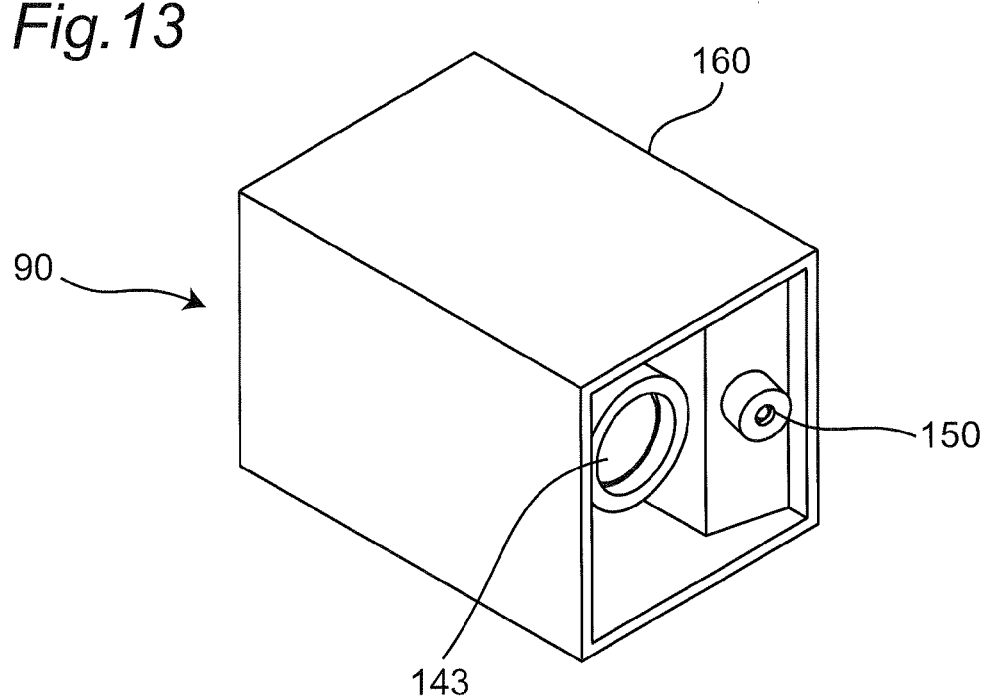
FIG. 13 is a perspective view of a recognition unit used in the first embodiment of the transcranial magnetic stimulation system.

The adjustment mechanism 66 is fixed to the horizontal frame 65 by fixing members 67. In the modification shown, the adjustment mechanism 66 has a rectangular frame 660 including front and rear vertical frame portions 660a and 660b and upper and lower horizontal frame portions 660c and 660*d*. The vertical frame portions 660*a* and 660*b* and the horizontal frame portions 660*c* and 660*d* have guide slots 661,662,663, and 664, respectively. The guide slots 661, 662,663, and 664 have slide blocks 665, 681, 666, and 683 fitted therein so that they move along the guide slots 661, 662,663, and 664, respectively. FIGS. 12A-12C show a partial enlarged view of the adjustment mechanism 66, in which the slide block 665 is indicated to have a main portion 680*a* and an engagement portion 680*b*. As shown in FIG. 12B, the main portion 680*a* has a width larger than that of the guide slot and the engagement portion 680*b* has substantially the same width as that of the guide slot, allowing the slide block 665 to move in the longitudinal direction of the guide slot 661 with the engagement portion 680*b* inserted in the guide slot 661. Likewise, the slide block 681 of the opposing right vertical frame portion 660*b* has a main portion 681*a* and an engagement portion 681*b*. The engagement portion 681*b* has substantially the same width as the guide slot 662, allowing the slide block 681 to move in the longitudinal direction along the guide slot 662 with the engagement portion 681*b* inserted in the guide slot 662. Although detailed descriptions will not be made, the slide blocks 682 and 683 associated with the upper and lower frame portions 660*c* and 660*d* have the same structure so that they can move in the respective longitudinal directions along the guide slots with the engagement portions thereof inserted in the associated guide slots.

The front and rear slide blocks 665 and 681 have throughholes 6650 and 6810 defined respective centers thereof and extending therethrough in the opposing direction, in which the cylindrical threaded shaft 684 is inserted for rotation. One end of the threaded shaft 684, e.g., a portion thereof projected from the front slide block 665, supports a knob 667 fixed thereto. The other end of the threaded shaft 684, e.g., a portion projected from the rear slide block 681, has a peripheral groove 6840 in which a C-ring 6841 is fitted. The slide blocks 682 and 683 associated with the upper and lower frame portions 660*c* and 660*d* have the same structure in each of which one end of the threaded shaft 685, e.g., a portion projected from the upper slide block, supports a knob fixed thereto and the other end of the threaded shaft 685, e.g., a portion projected from the lower slide block, has a peripheral groove in which a C-ring is fitted. This allows the paired front and rear slide blocks 665 and 681 and the paired upper and lower slide blocks 666 and 683 to move in the vertical and front-back directions as they are guided by the associated guide slots.

Central portions of the shafts 684 and 685 extend through the housing 160 of the recognition unit 90 and have respective external threads 684*a* and 685*a* defined thereon. Four walls 1600, 1601, 1602, and 1603 of the housing 160, through which the shafts 684 and 685 extend, securely support internally threaded members 690*a*, 690*b*, 691*a*, and 691*b*, respectively. The external thread 684*a* of the horizontally oriented shaft 684 is threaded in the internal threads of the internally threaded members 690*a* and 690*b* mounted on the front and rear walls 1600 and 1601 of the housing 160. Also, the external thread 685*a* of the vertically oriented shaft 685 is threaded in the internal threads 691*a* and 691*b* in the upper and lower walls 1602 and 1603 of the housing 160.

According to the magnetic stimulation system 1*c* so constructed, rotating the knob 667 of the shaft 684 extending in the front-rear direction causes the recognition unit 90 to move in the front-rear direction and rotating the knob 668 of the shaft 685 extending in the vertical direction causes the recognition unit 90 to move in the vertical direction, which in turn causes the camera 143 and the laser beam oscillator 150 of the recognition unit 90 to move in the vertical and front-rear directions. In use of the magnetic stimulation system 1*c*, the coil holder 10*c* is moved relative to the patient M wearing the helmet 64 into the optimum coil position of the patient M. Once positioned at the optimum coil position, the coil holder 10*c* is secured to the helmet 64. Then, the patient or helper rotates the knobs 667 and 668 to move the recognition unit 90 so that the optical axis of the laser beam oscillator 150 is oriented to the target mounted on the patient M, e.g., the marking (not shown) provided at the mostoid bone or convex portion behind his or her ear while viewing the images on the display (not shown).

After the camera 143 and the laser beam oscillator 150 are set at respective positions corresponding to the optimum coil position, the coil holder 10*c* is readily positioned at the optimum coil position simply by aligning the optical axis of the laser beam oscillator 150 on the target in the subsequent wearing of the helmet 64. Preferably, as shown in FIG. 12A the knob 667 has a scale 6670 marked on its peripheral surface and the slide block 665 adjacent the knob 667 has a reference 6671 marked thereon, allowing the knob to be set into a position corresponding to the optimum coil position. Although the recognition unit 90 is designed to be moved in the vertical and front-rear directions with respect to the head of the patient M in the modification, it may be designed to rotate about horizontal and vertical axes. Also, the camera 143 and the laser beam oscillator 150 may be designed so that their positions are independently adjusted.

Second Embodiment

Figure 14:
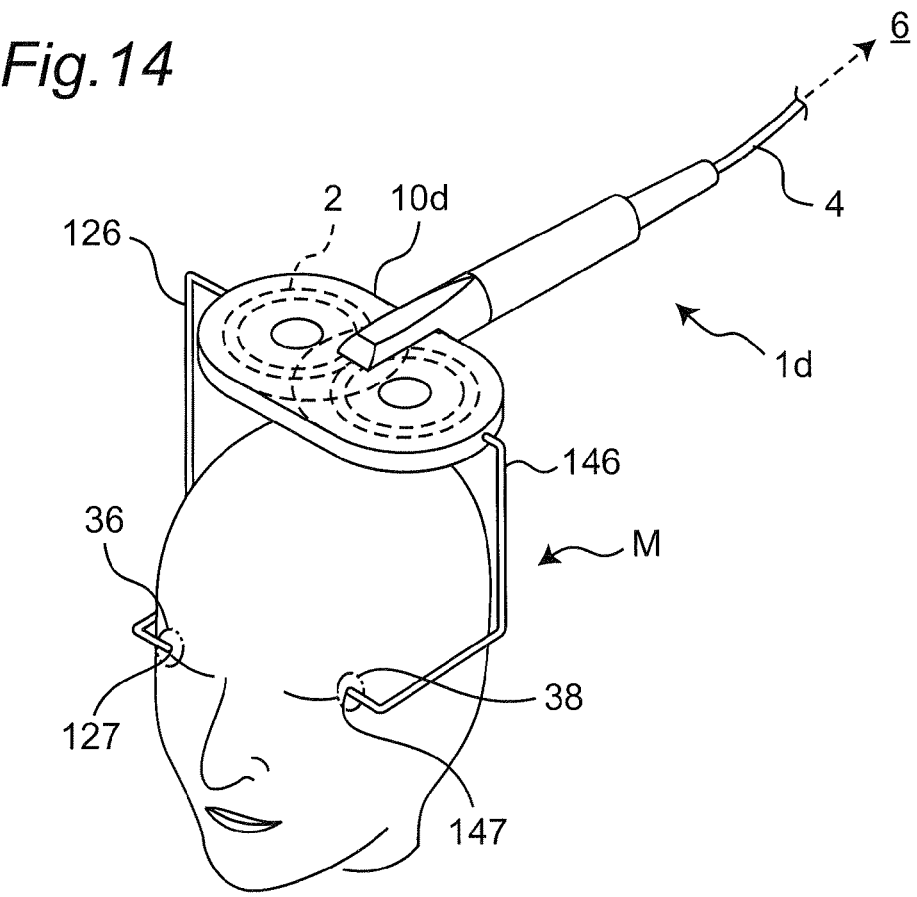
FIG. 14 is a perspective view showing a second embodiment of the transcranial magnetic stimulation system according to the invention.

Referring to FIG. 14, another embodiment will be described in which a part of the patient is used as a marking. In the followings, the corner of patient's eye is used as a positioning marking against which the coil holder is positioned. In the drawings, the major portions (except for the positioning portion) of the coil holder 10*d* are the same as those of the first embodiment and like reference numbers designate like or corresponding parts to eliminate duplicate descriptions.

As shown in FIG. 14, the coil holder 10*d* of the this embodiment has positioning arm members (positioning portions) 126 and 146 made of metal rod and provided at opposite longitudinal ends thereof. As shown in the drawings, the arm members 126 and 146 are extended outwardly from the opposite ends of the coil holder 10*d* and then bent several times so that the distal ends 127 and 147 of the arm members are brought into contacts with respective portions 36 and 38 of the patient M adjacent his or her corners of eyes where his or her left and right zygomatic bones are recessed This allows that the coils of the coil holder 10*d* are readily positioned at the optimum coil position of the patient M simply by positioning the distal ends 127 and 147 of the arm members 126 and 146 at the recessed portions of his or her zygomatic bones adjacent the eye corners. This arrangement eliminates any need to provide patient M with attachment such as pattern or object and therefore imposes less burden on patient.

Advantageously, an incorporation of an ultracompact CCD camera at the distal ends 127 and 147 of the arm members 126 and 146 allows the patient by himself or herself to place the coils 2 of the coil holder 10*d* at the optimum coil position while viewing the target positions or the recessed portions 36 and 38 of zygomatic bones adjacent eye corners through the display.

Third Embodiment

Figure 15:
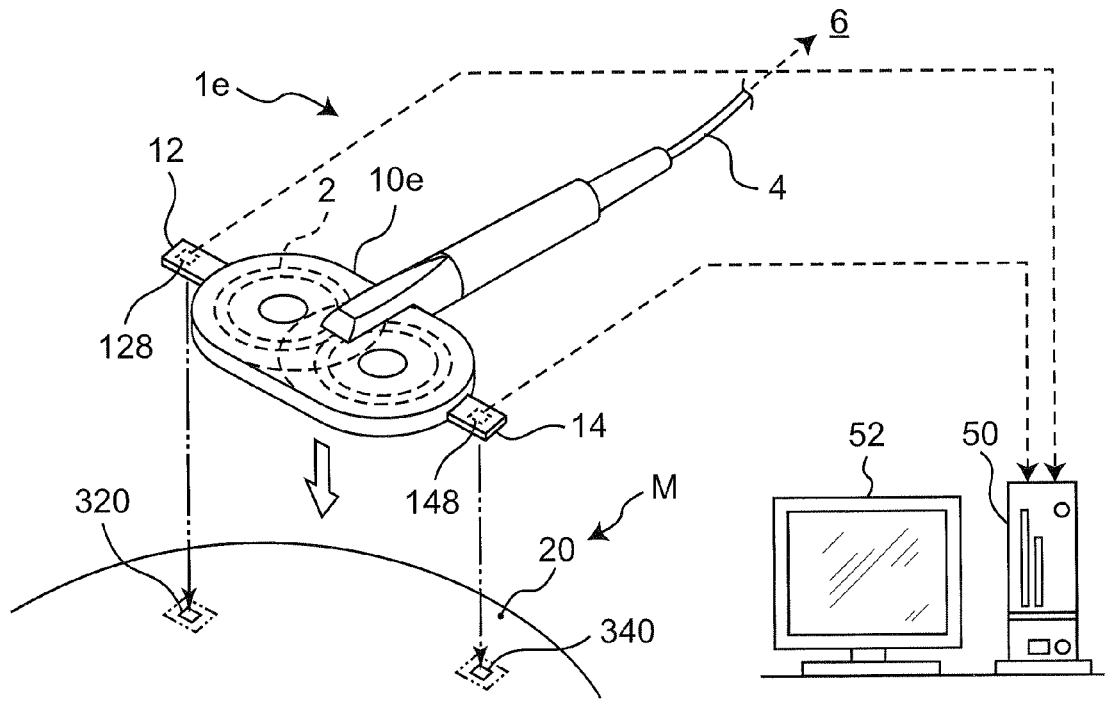
FIG. 15 is a perspective view showing a third embodiment of the transcranial magnetic stimulation system according to the invention.

Referring to FIG. 15, another embodiment will be described below which uses magnets fixed or implanted under the head skin of patient for the positioning of the coil holder. In the drawings, the major portions (except for the positioning portion) of the coil holder 10e are the same as those of the first embodiment and like reference numbers designate like or corresponding parts to eliminate duplicate descriptions.

As shown in FIG. 15, two magnets 320 and 340 (means for generating magnetic field) are provided at certain portions on or under the head skin 20 of the patient M. The coil holder 10e holds rectangular projections 12 and 14 mounted at longitudinal edge opposite end portions thereof and extending in parallel to the upper and lower surfaces of the coil holder 10e. The projections 12 and 14 support at bottom surfaces thereof magnetic sensors 128 and 148 (means for detecting magnetic field) for the detection of magnetic force from the magnets 320 and 340, respectively. A distance between the centers of the magnetic sensors 128 and 148 is set to the same as that of the magnets 320a and 340.

The magnetic stimulation system 1e of this embodiment has a converter 50 for converting outputs from the magnetic sensors 128 and 148 into electric signals with intensities corresponding to the detected magnetic forces of the magnets 320 and 340 and a display 52 for displaying the intensities of signals from the converter 50.

Figure 17:
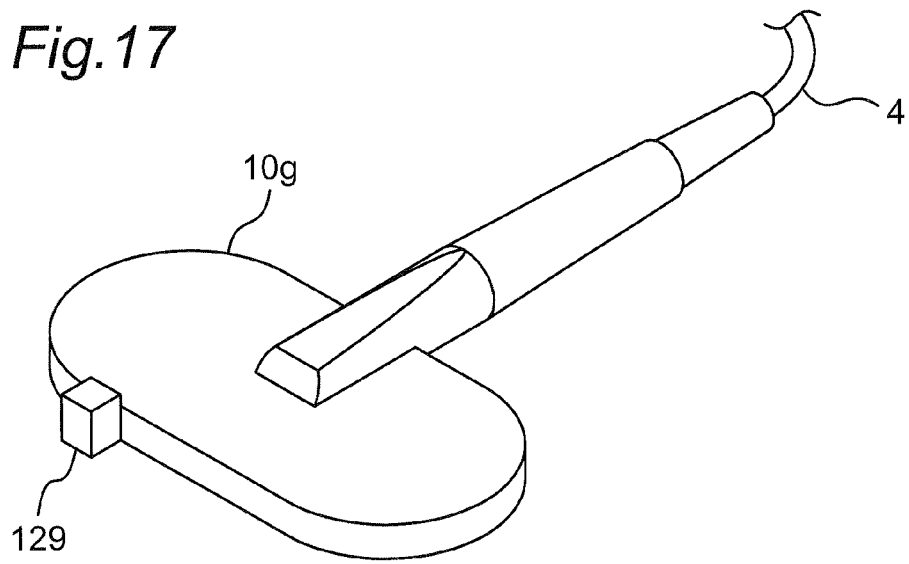
FIG. 17 is a perspective view showing another modification of the third embodiment of the transcranial magnetic stimulation system according to the invention.

With the arrangement, the patient can move the coil holder 10e into the optimum coil position where the signal intensities related to the magnets 320 and 340 take the maximum values, while viewing the display 52. This allows the patient to position the coil 2 at the optimum coil position without any help of helper. As shown in FIG. 17, only one magnetic sensor 129 is provided at the periphery of the coil holder if only one magnet (not shown) is mounted in the head skin of the patient.

According to the magnetic stimulation system in the first to third embodiments the coil holder 10 is moved and positioned on the patient's head surface by the patient M or the helper; however, this positioning procedures may be automated by a magnetic stimulation system equipped with a moving device or mechanism which will be described below.

Fourth Embodiment

Figure 18:
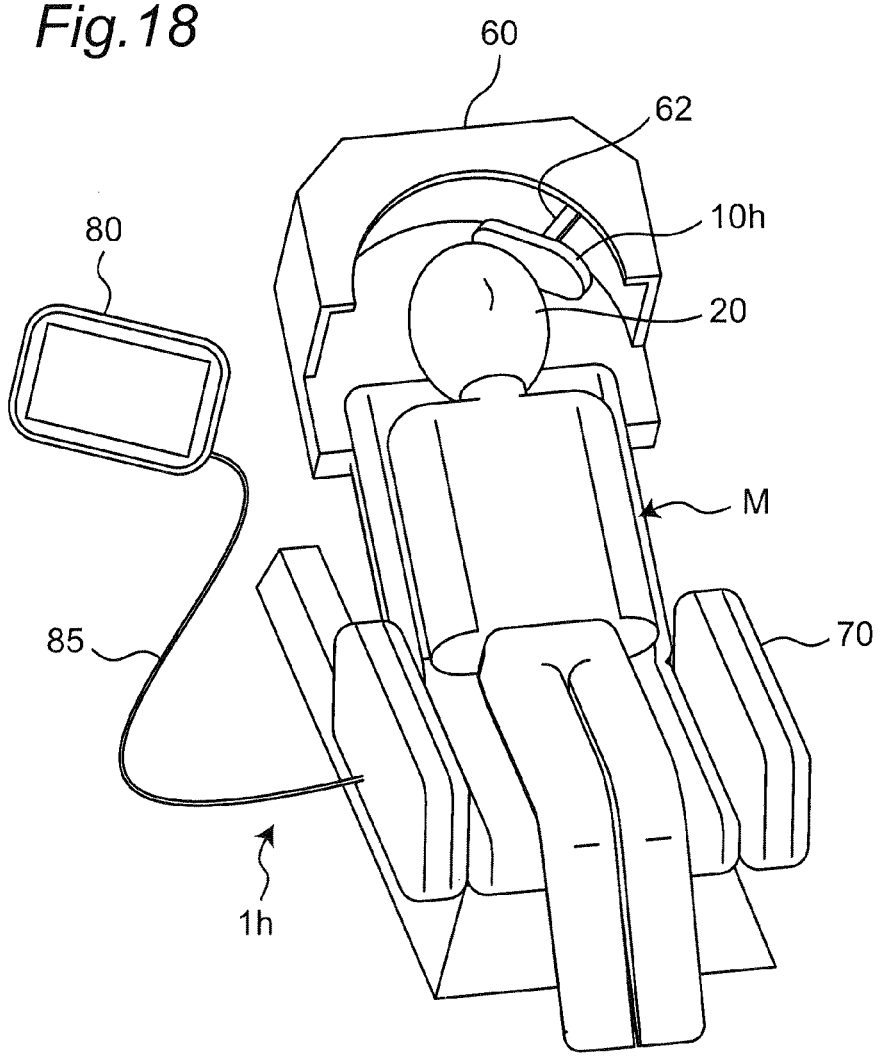
FIG. 18 is a perspective view showing a general construction of the fourth embodiment of the transcranial magnetic stimulation system according to the invention.

FIG. 18 shows the magnetic stimulation system 1h equipped with the moving device 60 or mechanism which is designed to move the coil holder 10h with the stimulation coil (not shown) along a spherical surface resembling the head surface 20 of patient M. The coil holder 10h is supported by a support member 62 which is capable of supporting it in a desired posture against the head surface 20 of patient M. The moving device 60 is positioned above the head of patient M so that it covers a part of the head of patient M. In the drawing, a medical chair 70 on which patient M lies on his or her back supports the moving device 60 which is electrically connected to a controller 80 or controlling means for controlling the moving device 60. Further, although not shown, the coil holder 10h supports on its bottom surface an image sensor or recognition means for automatically detecting the marking provide on the head surface 20 of patient M.

With the magnetic stimulation system 1g so constructed, the image sensor automatically recognizes the marking as it moves along the head surface of patient M and thereby positions the coil 2 of the coil holder 10g at the optimum coil position.

The marking recognition means is not limited to the image sensor. For example, the marking made of magnet can automatically be recognized using an output from a magnetic sensor.

According to the magnetic stimulation system of the embodiments 1-4, the stimulation coil can be positioned at the optimum coil position by positioning the coil holder against the marking or markings provided on or under the head surface of patient M, for example, mostoid bone behind his or her ear, allowing users such patient and helper to position the coil holder or coil without difficulty without skill.

REFERENCE NUMERALS LIST

1: transcranial magnetic stimulation system
2: stimulation coil
4: cable
6: magnetic stimulation controller
8, 70: chair
10: coil holder
12, 14: positioning projection (positioning portion)
20: head surface of patient
50: converter
52: display
60: moving device
32, 34: marking
143: camera
126, 146: guide rod
128, 148: magnetic sensor
150: laser beam oscillator
320, 340: magnet
M: patient

The invention claimed is:

1. A transcranial magnetic stimulation system, comprising:
   a magnetic field generator configured to provide magnetic stimulation against a portion of a patient's head,
   the magnetic field generator comprising a magnetic coil configured to generate a variable magnetic field, and a holder configured to hold the magnetic coil,
   wherein the holder comprises a positioning portion configured to position the holder against a marking provided on the patient's head so, and
   wherein the transcranial magnetic stimulation system further comprises a recognition member having at least one imaging device provided adjacent to the holder and configured to recognize the marking, such that the coil is positioned in a predetermined posture against the portion by aligning an optical axis of the imaging device with the marking,
   wherein the magnetic coils and the imaging device are attached to the holder.

2. The transcranial magnetic stimulation system according to claim 1, wherein the coil is adapted to be positioned in the predetermined posture against the portion by aligning the positioning portion with the marking on the patient's head.

3. The transcranial magnetic stimulation system according to claim 1, wherein the coil is configured to be aligned in the predetermined posture against the portion by rolling the imaging device about a contact position between the patient's head and a lower surface of the holder, opposing the patient's head, until the optical axis is aligned with the marking.

4. The transcranial magnetic stimulation system according to claim 1, further comprising:

an optical device provided adjacent to the imaging device and configured to emit a directional light beam, wherein the coil is configured to be aligned in the predetermined posture against the portion by aligning an intersection, of the directional light beam and the optical axis of the imaging device, with the marking.

5. The transcranial magnetic stimulation system according to claim 1, further comprising:

a moving mechanism configured to move the holder on and along a surface of the patient's head; and a controller configured to control the moving mechanism in accordance with an output from the recognition member to automatically position the positioning portion against the marking.

6. The transcranial magnetic stimulation system according to claim 1, wherein the marking comprises at least one of a pattern adapted to be applied on a surface of the patient's head, an object adapted to be attached to the surface of the patient's head, and an object adapted to be implanted under the surface of the patient's head.

7. The transcranial magnetic stimulation system according to claim 1, wherein the marking comprises an object adapted to be attached to the surface of the patient's head or implanted under a surface of the patient's head;

the object is configured to generate a magnetic field; and the recognition member further comprises a magnetic sensor configured to detect the magnetic field.

8. The transcranial magnetic stimulation system according to claim 1, wherein the marking comprises an object adapted to be attached to a surface of the patient's head or implanted under the surface of the patient's head;

the object is configured to generate a radio signal.

9. The transcranial magnetic stimulation system according to claim 1, wherein the marking comprises an object adapted to be attached to a surface of the patient's head or implanted under the surface of the patient's head;

the object has a visible configuration.

* * * * *